US012754183B2

(12) United States Patent
Zheng et al.

(10) Patent No.: US 12,754,183 B2
(45) Date of Patent: Oct. 6, 2026

(54) LIPID-BASED PROBES FOR EXTRACELLULAR ISOLATION

(71) Applicant: THE PENN STATE RESEARCH FOUNDATION, University Park, PA (US)

(72) Inventors: Si-Yang Zheng, University Park, PA (US); Yuan Wan, University Park, PA (US); Gong Cheng, University Park, PA (US)

(73) Assignee: The Penn State Research Foundation, University Park, PA (US)

(*) Notice: Subject to any disclaimer, the term of this patent is extended or adjusted under 35 U.S.C. 154(b) by 844 days.

(21) Appl. No.: 16/466,511

(22) PCT Filed: Dec. 5, 2017

(86) PCT No.: PCT/US2017/064634
§ 371 (c)(1),
(2) Date: Jun. 4, 2019

(87) PCT Pub. No.: WO2018/106648
PCT Pub. Date: Jun. 14, 2018

(65) Prior Publication Data
US 2020/0080997 A1 Mar. 12, 2020

Related U.S. Application Data

(60) Provisional application No. 62/430,161, filed on Dec. 5, 2016.

(51) Int. Cl.
*G01N 33/543* (2006.01)
*G01N 21/64* (2006.01)

(52) U.S. Cl.
CPC ... *G01N 33/54313* (2013.01); *G01N 21/6428* (2013.01); *G01N 33/54366* (2013.01); *G01N 2021/6439* (2013.01)

(58) Field of Classification Search
CPC ......... G01N 33/54313; G01N 21/6428; G01N 33/54366; G01N 2021/6439
(Continued)

(56) References Cited

U.S. PATENT DOCUMENTS 6,132,764 A 10/2000 Li et al.
8,268,264 B2 * 9/2012 Lenz ...................... B03C 1/288 422/68.1
(Continued)

FOREIGN PATENT DOCUMENTS

CN 102084000 A 6/2011
CN 104302667 A 1/2015
(Continued)

OTHER PUBLICATIONS

Hermanson, G.T. "Chapter 11 (Strept)avidin-Biotin Systems" Bioconjugate Techniques. 3rd ed., edited by G.T. Hermanson, pp. 465-505. London: Academic Press, 2013 (Year: 2013).*
(Continued)

*Primary Examiner* — Bao-Thuy L Nguyen
*Assistant Examiner* — Stefanie J. Kirwin
(74) *Attorney, Agent, or Firm* — Buchanan Ingersoll & Rooney PC

(57) ABSTRACT

Lipid-based probes and systems therewith to capture and isolate extracellular vesicles from a sample are disclosed. The system can include a labelling probe-capture probe combination or an immobilized labelling probe on a surface of a substrate or a device including the immobilized labelling probe on a surface of a substrate. The labelling probe can include a lipid tail for insertion in the lipid bilayer membrane of extracellular vesicles. The labelling probe can further include a tag that can be readily combine with a capture probe or a high affinity component to bind to a substrate surface to immobilize the labelling probe, and a
(Continued)

spacer between the lipid tail and tag or high affinity component.

19 Claims, 4 Drawing Sheets

Specification includes a Sequence Listing.

(58) Field of Classification Search
USPC .......................................................... 424/450
See application file for complete search history.

(56) References Cited

U.S. PATENT DOCUMENTS

| | | | | |
|---|---|---|---|---|
| 2015/0010913 A1* | 1/2015 | Ohta | G01N 33/574 530/387.9 |
| 2015/0233800 A1* | 8/2015 | Dangerfield | G01N 1/30 435/5 |
| 2016/0169876 A1 | 6/2016 | Ichiki et al. | |
| 2016/0349246 A1* | 12/2016 | Fujii | G01N 33/5432 |

FOREIGN PATENT DOCUMENTS

| | | | | |
|---|---|---|---|---|
| CN | 105723221 A | 6/2016 | |
| WO | 2009/100029 A1 | 8/2009 | |
| WO | 2010/065765 A2 | 6/2010 | |
| WO | WO-2015068772 A1 * | 5/2015 | C12Q 1/6804 |
| WO | 2016/152786 A1 | 3/2018 | |

OTHER PUBLICATIONS

Kuhn, P., Eyer, K., Robinson, T., Schmidt, F.I., Mercer, J., Dittrich, P.S. A facile protocol for the immobilisation of vesicles, virus particles, bacteria, and yeast cells, Integrative Biology 4 (2012) 1550-1555 (Year: 2012).*

Thery C, Clayton A, Amigorena S, Raposo G (2006), "Isolation and Characterization of Exosomes from Cell Culture Supernatants and Biological Fluids", Current Protocols in Cell Biology. vol. 30, Issue 1, pp. 3.20.1-14.7.35. (Year: 2006).*

Schageman J, Zeringer E, Li M, Barta T, Lea K, Gu J, Magdaleno S, Setterquist R, Vlassov AV (2003), "The Complete Exosome Workflow Solution: From Isolation to Characterization of RNA Cargo", BioMed Research International, vol. 213, pp. 1-15. (Year: 2003).*

Kuhn P, Eyer K, Robinson T, Schmidt FI, Mercer J, Dittrich PS (2012) "A facile protocol for the immobilization of vesicles virus particles, bacteria, and yeast cells", Integrative Biology, 4, pp. 1550-1555 (Year: 2012).*

Wan Y, Cheng G, Liu X, Hao SJ, Nisic M, Zhu CD, Xia YQ, Li WQ, Wang ZG, Zhang WL, Rice SJ, Sebastian A, Albert I, Belani CP, Zheng SY "Rapid magnetic isolation of extracellular vesicles via lipid-based nanoprobes" Nature Biomedical Engineering, 1, 0058, published Apr. 10, 2017, 11 pages (Year: 2017).*

Schäfer B, Orbán E, Borics A, Huszár K, Nyeste A, Welker E, Tömböly C. Preparation of semisynthetic lipoproteins with fluorescent cholesterol anchor and their introduction to the cell membrane with minimal disruption of the membrane. Bioconjugate Chemistry. Oct. 16, 2013;24(10):1684-97. (Year: 2013).*

Jeppesen DK, Hvam ML, Primdahl-Bengtson B, Boysen AT, Whitehead B, Dyrskjøt L, Ørntoft TF, Howard KA, Ostenfeld MS. Comparative analysis of discrete exosome fractions obtained by differential centrifugation. Journal of extracellular vesicles. Jan. 1, 2014;3(1):25011. (Year: 2014).*

Hink MA, Griep RA, Borst JW, Van Hoek A, Eppink MH, Schots A, Visser AJ. Structural dynamics of green fluorescent protein alone and fused with a single chain Fv protein. Journal of Biological Chemistry. Jun. 9, 2000;275(23):17556-60. (Year: 2000).*

International Search Report issued in International Application No. PCT/US2017/064634 mailed Apr. 20, 2018.

Written Opinion issued in International Application No. PCT/US2017/064634 mailed Apr. 20, 2018.

Office Action for Chinese Application 201780075420.8 dated Dec. 14, 2023.

* cited by examiner

SEQUENCE LISTING

<160> NUMBER OF SEQ ID NOS: 10

<210> SEQ ID NO 1
<211> LENGTH: 21
<212> TYPE: DNA
<213> ORGANISM: Unknown
<220> FEATURE:
<223> OTHER INFORMATION: Primer used for KRAS analysis

<400> SEQUENCE: 1
aaggcctgct gaaaatgact g 21

<210> SEQ ID NO 2
<211> LENGTH: 21
<212> TYPE: DNA
<213> ORGANISM: Unknown
<220> FEATURE:
<223> OTHER INFORMATION: Primer used for KRAS analysis

<400> SEQUENCE: 2
tcacaatacc aagaaaccca t 21

<210> SEQ ID NO 3
<211> LENGTH: 25
<212> TYPE: DNA
<213> ORGANISM: Unknown
<220> FEATURE:
<223> OTHER INFORMATION: Primer used for EGFR Exons 19 analysis

<400> SEQUENCE: 3
gcaatatcag ccttaggtgc ggctc 25

<210> SEQ ID NO 4
<211> LENGTH: 26
<212> TYPE: DNA
<213> ORGANISM: Unknown
<220> FEATURE:
<223> OTHER INFORMATION: Primer used for EGFR Exons 19 analysis

<400> SEQUENCE: 4
catagaaagt gaacatttag gatgtg 26

<210> SEQ ID NO 5
<211> LENGTH: 20
<212> TYPE: DNA
<213> ORGANISM: Unknown
<220> FEATURE:
<223> OTHER INFORMATION: Primer used for EGFR Exons 21 analysis

<400> SEQUENCE: 5
tgcagagctt cttcccatga 20

<210> SEQ ID NO 6
<211> LENGTH: 21
<212> TYPE: DNA
<213> ORGANISM: Unknown
<220> FEATURE:
<223> OTHER INFORMATION: Primer used for EGFR Exons 21 analysis

<400> SEQUENCE: 6
gcatgtgtta aacaatacag c 21

<210> SEQ ID NO 7
<211> LENGTH: 21
<212> TYPE: DNA
<213> ORGANISM: Unknown

-continued

```
<220> FEATURE:
<223> OTHER INFORMATION: Primer used for Exon 19 next PCR analysis

<400> SEQUENCE: 7

taaaattccc gtcgctatca a                                              21


<210> SEQ ID NO 8
<211> LENGTH: 18
<212> TYPE: DNA
<213> ORGANISM: Unknown
<220> FEATURE:
<223> OTHER INFORMATION: Primer used for Exon 19 next PCR analysis

<400> SEQUENCE: 8

atgtggagat gagcaggg                                                  18


<210> SEQ ID NO 9
<211> LENGTH: 21
<212> TYPE: DNA
<213> ORGANISM: Unknown
<220> FEATURE:
<223> OTHER INFORMATION: Primer used for Exon 21 next PCR analysis

<400> SEQUENCE: 9

cagcagggtc ttctctgttt c                                              21


<210> SEQ ID NO 10
<211> LENGTH: 21
<212> TYPE: DNA
<213> ORGANISM: Unknown
<220> FEATURE:
<223> OTHER INFORMATION: Primer used for Exon 21 next PCR analysis

<400> SEQUENCE: 10

gaaaatgctg gctgacctaa a                                              21
```

LIPID-BASED PROBES FOR EXTRACELLULAR ISOLATION

STATEMENT REGARDING FEDERALLY SPONSORED RESEARCH

This invention was made with government support under Grant No. CA174508 awarded by the National Institutes of Health. The Government has certain rights in the invention.

STATEMENT REGARDING SEQUENCE LISTINGS

A Sequence Listing compliant with World Intellectual Property Organization (WIPO) Standard ST.25 is provided herewith and the entirety of this sequence listing is incorporated by reference herein. The Sequence Listing that is incorporated by reference herein was e-filed at the USPTO using Patent Center as a .TXT file named 0073605000779.txt (3 KB in size, created on Aug. 11, 2024).

CROSS-REFERENCE TO RELATED APPLICATION

This application is the U.S. National Phase under 35 U.S.C. § 371 of International Application No. PCT/US2017/064634 filed Dec. 5, 2017, which claims the benefit of U.S. Provisional Application No. 62/430,161 filed Dec. 5, 2016, the entire contents of each are hereby incorporated by reference herein.

TECHNICAL FIELD

The present invention relates to lipid-based probes and systems therewith to capture and isolate extracellular vesicles from a sample. The lipid probe can include a lipid tail, a spacer and a tag and/or can be immobilized on a surface. The systems can isolate extracellular vesicles from a sample such as body fluid from a human patient.

BACKGROUND

Extracellular vesicles (EVs)—which include exosomes, microvesicles and apoptotic bodies—are cell-derived lipid-bilayer-enclosed structures, with sizes ranging from 30 to 5,000 nm. In the past decade, EVs have emerged as important mediators of cell communication because they serve as vehicles for the intercellular transmission of biological signals capable of altering cell function and physiology. In particular, exosomes—that is, EVs with diameters of approximately 30-150 nm, released on fusion of multi-vesicular bodies with the plasma membrane—containing cell and cell-state specific proteins and nucleic acids are secreted by many cell types and have been identified in diverse body fluids. Although the biogenesis of exosomes is not yet fully understood, growing evidence indicates that such nanoscale EVs (nEVs) can regulate tumour immune responses, initiate formation of the pre-metastatic niche, determine organotropic metastasis and contribute to chemo-therapeutic resistance. nEVs are thus potential targets for therapeutic intervention in cancer, and are promising as autologous drug vehicles capable of overcoming pharmacological barriers. They are also increasingly recognized as non-invasive diagnostic and prognostic tumour markers. Hence, it is highly desirable to isolate nEVs rapidly for downstream molecular analyses.

However, approaches reported for the isolation of nEVs—such as ultracentrifugation, immunoisolation, polymer-based precipitation and filtration—involve lengthy protocols, and can lead to impurities and nEV damage. Hence, there is a continuing need for methods and devices that can effectively isolate extracellular vesicles including nanoscale EVs.

SUMMARY OF THE DISCLOSURE

Advantages of the present invention include lipid-based probes and systems therewith to capture and isolate extracellular vesicles from a sample. The system can include a labelling probe-capture probe combination or an immobilized labelling probe on a surface of a substrate or a device including the immobilized labelling probe on a surface of a substrate of the device.

These and other advantages are satisfied, at least in part, by a method of isolating extracellular vesicles from a sample by contacting a labelling probe with a sample comprising extracellular vesicles having a lipid bilayer, wherein the labelling probe is configured to combine with the lipid bilayer of the extracellular vesicles so as to label the extracellular vesicles. The labeled extracellular vesicles can be captured with a capture probe configured to combine with the labelling probe. The labeled extracellular vesicles captured with the capture probe can then be isolated from the sample.

Another aspect of the present method of isolating extracellular vesicles from a sample by contacting a sample comprising extracellular vesicles with a surface of a substrate having a labelling probe immobilized thereon. The labelling probe is configured to combine with a lipid bilayer of the extracellular vesicles so as to immobilize the extracellular vesicles on the surface of the substrate. The labelling probe can be covalently bound or non-covalently bound to the surface of the substrate.

In yet another aspect of the present disclosure, a device for isolating extracellular vesicles from a sample can include a substrate surface having a labelling probe immobilized thereon. The device further includes a fluid flow pathway configured to provide a flow path for a sample comprising extracellular vesicles to contact the substrate surface. In some embodiments, the device can include a first electrode comprising the vesicle immobilizing surface of the substrate and a second electrode having an opposite polarity than the first electrode, the device being configured to apply an electric field to the sample using the first electrode and the second electrode.

In accordance with embodiments of the present disclosure, the present invention, the isolated EVs can also be extracted and analyzed for its contents such as for lipid, protein and nucleic acid contents using typical procedures. For example, after isolating and, in certain embodiments, releasing the EVs, nucleotides can be extracted from the isolated and/or released extracellular vesicles. A structure and/or a function of the extracted contents, e.g., nucleotides, proteins, lipids, can then be analyzed. Alternatively, a parameter dependent on a concentration of one or more of the contents of extracellular vesicles immobilized on the surface of a substrate can be measured.

Embodiments include one or more of the following features individually or combined. For example, in some embodiments, the labelling probe can include a lipid tail, a spacer and a tag. Lipid tails useful for labelling probes of the present disclosure include those that can readily insert themselves in the lipid bilayer membrane of extracellular vesicles. Lipid spacers useful for labelling probes of the present disclosure include those that space the lipid tails from the tag and facilitate binding the tag with the capture probe or substrate surface for immobilizing the labelling probe. Tags that are useful for the present disclosure include those than can be readily combinable with a capture probe or substrate surface to immobilize the labelling probe. In some embodiments, the labeling probe includes a component that has a high affinity to a substrate surface. In other embodiments, the capture probe is a particle coated with a binding molecule having a high binding affinity for the tag, e.g., a biotin. Such particles include magnetic sub-micrometer particles coated with a deglycosylated version of an avidin protein, an example of which is NeutrAvidin™ protein provided by Fisher Scientific. In still further embodiments, the methods include releasing the labeled extracellular vesicles from the capture probe. This can be done, for example, by displacing the labeled extracellular vesicles from the capture probe by using a compound with a higher affinity for the capture probe than the tag on the labelling probe used to label the extracellular vesicles. Alternatively, or in combination, releasing the labeled extracellular vesicles from the capture probe or a substrate surface can include, when the labelling probe includes a spacer, by degradation of spacer.

In other embodiments, the substrate surface can be from a substrate of silica, a polymer, such as agarose, cellulose, dextran, polyacrylamide, latex, etc. In some other embodiments, the extracellular vesicles immobilized on the surface can be contacted with a lipid bilayer permeant fluorescent marker. Advantageously, the fluorescent marker has a high binding affinity for a given molecule in the extracellular vesicles immobilized on the surface. In still further embodiments, a parameter dependent on a concentration of one or more of the contents of extracellular vesicles immobilized on the surface can be measured such as total fluorescence intensity of the fluorescent marker bound to the given molecule in the extracellular vesicles immobilized on the surface.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIG. 3*c* shows isolation efficiency and incubation time of LP-labelled MDA-MB-231 nEVs and CPs; mean±s.e.m. (n=5). FIG. 3*d* is a plot of isolation efficiency of nEVs from healthy-donor plasma samples as a function of LP amount. Error bars, mean±s.e.m. (n=3).

DETAILED DESCRIPTION OF THE DISCLOSURE

Figure 1:
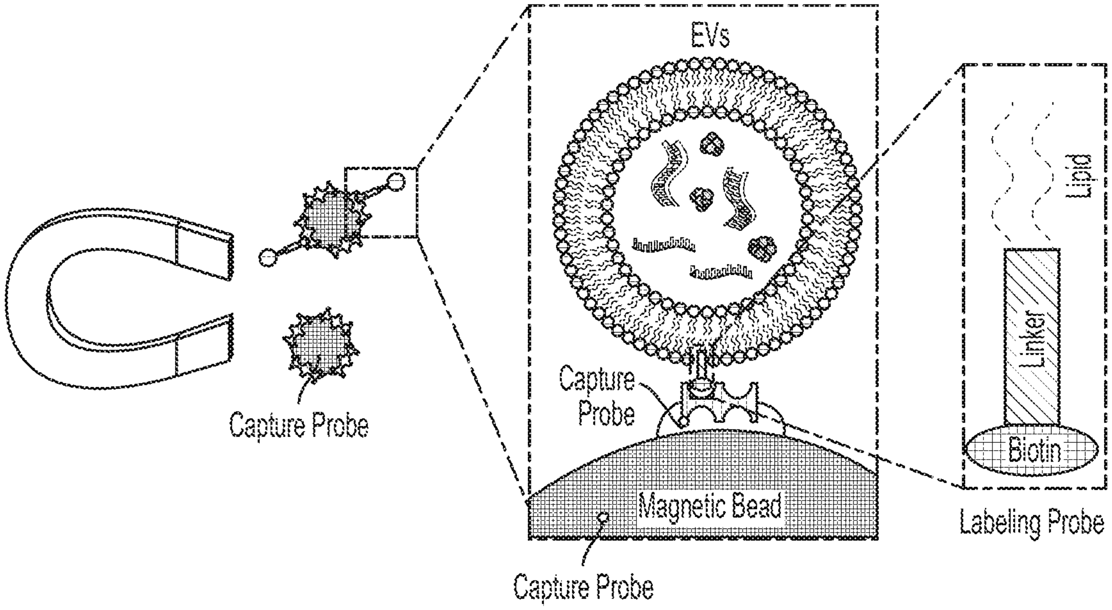
FIG. 1 illustrates a labelling probe and a capture probe and a method of isolating extracellular vesicles according to one aspect of the present disclosure.

The present disclosure relates to a lipid-based probe system that can be used to capture and isolate extracellular vesicles such as nEVs from a sample. The system can include a labelling probe (LP), which can include a lipid tail and a spacer. In one aspect of the present disclosure, the system includes a capture probe, which can be a particle that is mobile in the sample (e.g., FIG. 1) or the system can include a substrate that is fixed (e.g., FIG. 2) such that the LP is immobilized on a surface of a substrate and the sample is contacted with the fixed substrate to capture the EVs.

In an aspect of the present disclosure, extracellular vesicles can be isolated from a sample by contacting a labelling probe with a sample comprising extracellular vesicles. As explained in the Background section, extracellular vesicles have a lipid bilayer membrane. The labelling probes of the present disclosure are configured to combine with the lipid bilayer of the extracellular vesicles so as to label the extracellular vesicles. The labeled extracellular vesicles can be captured with a capture probe configured to combine with the labelling probe through a tag. The labeled extracellular vesicles captured with the capture probe can then be isolated.

In another aspect of the present disclosure, extracellular vesicles can be isolated from a sample by contacting a sample comprising extracellular vesicles with a surface of a substrate having a labelling probe immobilized thereon. Advantageously, the labelling probe is configured to combine with a lipid bilayer of the extracellular vesicles so as to immobilize the extracellular vesicles on the surface of the substrate. In some embodiments, the labeling probe includes a component that has a high affinity to a substrate surface and thus can be immobilized on the surface of the substrate by covalent or non-covalent bonding of the component. For example, the labelling probe can be covalently bound to a substrate surface by an amine conjugation from an amine tagged labelling probe onto an aldehyde group on the substrate surface. The labelling probe can be non-covalently bound onto the substrate as well, e.g., nucleic acid hybridization, for example lipid-PEG-ssDNA hybridizes with the other immobilized ssDNA, etc.

Lipid tails useful for labelling probes of the present disclosure include those that can readily insert themselves in the lipid bilayer membrane of extracellular vesicles. Such lipid tails include, for example, triglycerides, phospholipids such as mono-acyl lipid (C18), diacyl lipid (DSPE), steroids such as cholesterol, and any combination thereof. Additional useful lipid tails include fatty acids, glycerolipids, glycerophospholipids, sterol lipids, prenol lipids, sphingolipids, saccharolipids, polyketides, eicosanoids, their derivatives, and any combination thereof.

Lipid spacers useful for labelling probes of the present disclosure include those that space or link lipid tails from the tag or substrate surface and facilitate binding the labelling probe with the capture probe or substrate surface. Such lipid spacers include, for example, DNA, peptides, polymers, such as poly(ethylene oxide) (PEO), poly(propylene oxide) (PPO), poly(lactide-co-glycolide) (PLGA), polyacids such as poly(acrylic acid), poly(methacrylic acid), poly(2-ethyl acrylic acid) (PEAAc) and poly(2-propylacrylic acid), polybase such as polyl(N,N'-diethylaminoethyl methacrylate) (PDEAEMA), and block copolymers thereof, chitosan, alginate, nucleic acid, peptide, and other hydrophilic, non-charged materials with certain lengths, and any combination thereof. In some embodiments, the lipid spacers can have monomeric units of greater than 0 and up to 20,000 units, e.g., in arrange of about 10 to about 10,000 monomeric units such as a range of 50 to about 100. In other embodiments, the lipid spacer can have a length of greater than 0 and up to about 200 nm, e.g., 1-100 nm such as 3-80 nm.

The labelling probes of the present disclosure are configured to be captured by a capture probe or immobilized on a surface of substrate. The capture by a capture probe can achieved through a tag of the labelling probe. Tags that are useful for the present disclosure include those than can be readily combinable with a capture probe or substrate surface to immobilize the labelling probe. For example, such tag-capture probe combination can include a biotin tag that can be combined with NeutrAvidin™ (NA), which can be obtained from Thermo Fisher Scientific or Life Technologies, on the capture probe on surface substrate. Other tag-capture probe combinations include nucleic acid hybridization, aptamer and corresponding target, protein-protein interaction, and other molecular systems with specific high binding affinity, and any combination thereof. Other tag-capture probe combinations include His-tag and immobilized metal affinity chromatography matrices or magnetic beads, reactive dibenzylcyclootyne (DBCO) groups and azide molecules via copper-free click chemistry. The tag-capture probe combinations can also be used to immobilize a labeling probe on a substrate surface wherein the substrate surface has a complementary compound to the tag of the labelling probe.

Capture probes useful for the present disclosure include particles that can be readily isolated such as a magnetic particle, a metal particle, a charged particle, a plastic or ceramic particle, etc. and any combinations thereof. The capture probe includes a complimentary compound to bind the tag of the labelling probe such as NA, or an antigen on the surface thereof. Substrates used to immobilize lipid probes of the present disclosure can be made or plastic, glass, silica, ceramic and metals or any combination thereof and include a complimentary compound to bind the tag of the labelling probe.

Samples containing extracellular vesicles (EVs and/or nEVs) can include body fluid, such as tear, blood plasma, urine, ascites, etc. from a subject such as a human patient or other mammalian subject or from an extracellular vesicles culture.

Advantageously, the methods of the present disclosure can isolate EVs with high efficiency. For example, the methods of the present disclosure can have an isolation efficiency (i.e., the percentage of isolated EVs relative to the total amount available for isolation in a particular sample) of greater than 40%, such as greater than about 50%, about 60% and even greater than about 70% and about 80%. Isolating the labeled extracellular vesicles captured with the capture probe can be readily achieved by using a magnetic field when the capture probe is magnetic, or by antibodies, or by precipitation, size-based filtration, or by chromatography or by other forces such as electrostatic force, dielectrophoretic force, gravity, and centrifugal force, e.g., centrifugation such as ultracentrifugation.

Once isolated, the isolated EVs can be released. This can be done, for example, by using a compound with a higher affinity for the capture probe or the substrate surface than the tag on the labelling probe used to label the extracellular vesicles. Alternatively, the isolated EVs can be released by ion exchange chromatography, degradation of the spacer in spacer containing labelling probes. For example, if the labelling probe contains nucleic acid or peptide as spacer, the captured extracellular vesicles also can be released by degradation of nucleic acid or peptide, denaturation of nucleic acid, competitive hybridization of nucleic acids.

The isolated EVs can also be extracted and analyzed for its contents such as for lipid, protein and nucleic acid contents using typical procedures. For example, after isolating and in certain embodiments, releasing the EVs, lipids, proteins and nucleotides can be extracted from the isolated and/or released extracellular vesicles. A structure and/or a function of the extracted contents can then be analyzed. For example, DNA and RNA can be extracted from isolated nEVs followed by agarose gel electrophoresis to confirm the presence of RNA and DNA and fragments thereof. Alternatively, a parameter dependent on a concentration of one or more of the contents of extracellular vesicles immobilized on the surface of a substrate can be measured.

In an aspect of the present disclosure, a method of isolating nEVs includes use of a lipid-based probe system. The system for this embodiment includes a labelling probe (LP) and a capture probe (CP) sometimes referred to herein as a lipid nanoprobe (LNP). The LP can be composed of a lipid tail for nEV membrane insertion, a spacer such as a polyethylene glycol (PEG) spacer (about 45 ethylene oxide units, corresponding to ~156 Å of spacer length) for increasing reagent solubility, and a tag such as a biotin tag for subsequent capture and isolation of labelled nEVs. FIG. 1 illustrates a labelling probe having a biotin tag, linker (lipid spacer) and lipid tail. Three embodiments of labelling probes with three different lipid tails are described below to further aid in understanding aspects of the present disclosure.

We first compared the labelling efficiency among fluorescein isothiocyanate (FITC)-conjugated PEGylated monoacyl lipid (C18), diacyl lipid (DSPE) and cholesterol. Because both cell membranes and EV membranes are lipid bilayers, to facilitate evaluation we used $10^7$ breast adenocarcinoma MDA-MB-231 cells in Diluent C or 5% human albumin in phosphate-buffered saline. Although the presence of human albumin significantly decreased the fluorescence intensity of cells labelled with PEGylated lipids compared with the fluorescence intensity of the Diluent-C group ($P<0.05$; two-tailed t-test), the three lipids showed differential labelling efficiencies in the presence of albumin. The average fluorescence intensity of C18-labelled cells in 5% human albumin was slightly higher than that of cells labelled with DSPE, but there was no significant difference between the two groups. Considering that diacyl lipids have been widely used for the manipulation of cells and that the mechanism is known, we chose DSPE-PEG-biotin as the LP for the following studies.

NA-coated magnetic sub-micrometre particles (MMPs) served as the CP and enabled capture and isolation of nEVs in a suspension of a sample. The MMPs were prepared as a monodisperse suspension with a mean size of 465.4 nm. The MMPs had a negative zeta potential of −32.0 mV, arising from their silica shell. After aminosilane modification, absorption peaks at 2,920 $cm^{-1}$ and 2,852 $cm^{-1}$ in the spectra of Fourier transform infrared spectroscopy, associated with the stretching vibration of methylene groups in silane, indicated the immobilization of amine groups. Accordingly, the value of the zeta potential shifted to 9.6 mV and then decreases to −17.7 mV once isothiocyanate was conjugated. The surface-modification process was finalized with the covalent immobilization of NA (see Experimental section below).

Figure 3A:
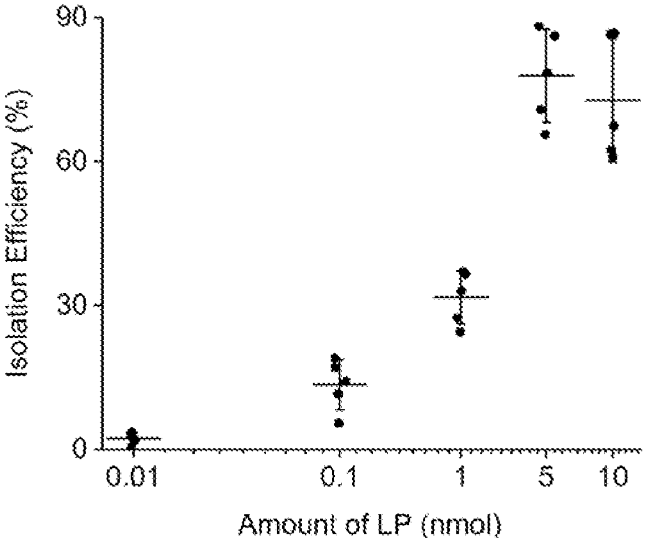
FIGS. 3*a*-3*d* are plots of isolation efficiency. The plots show isolation efficiency for MDA-MB-231 nEVs as a function of LP quantity (FIG. 3*a*), incubation time (FIG. 3*b*) of the LPs with model samples.
Figure 3B:
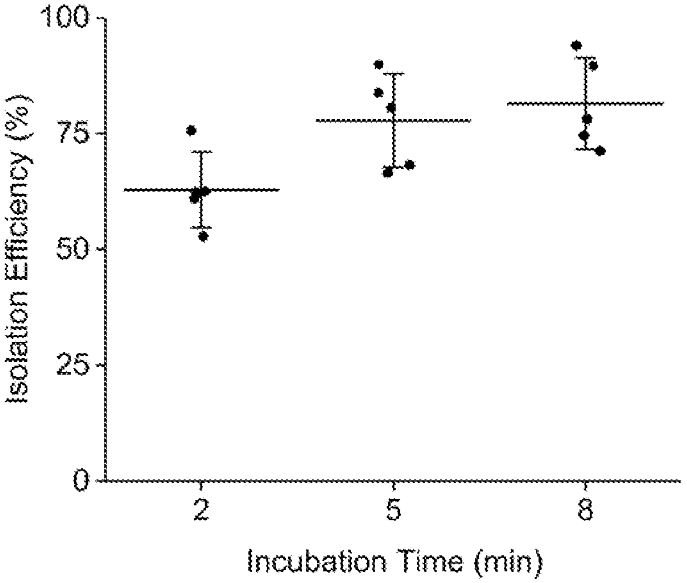
Figure 3C:
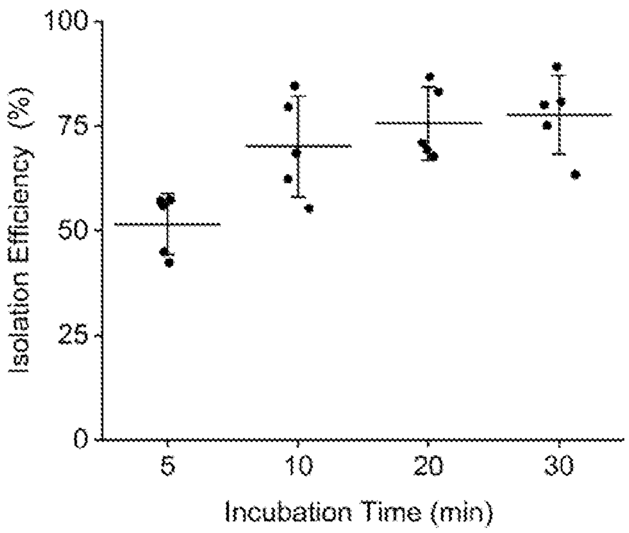

Nanoscale extracellular vesicles from MDA-MB-231 cells were isolated via ultracentrifugation, and identified by electron microscopy. The isolated nEV population mainly included vesicles with diameters of 30-200 nm, exhibiting the characteristic saucer-shaped morphology under electron microscopy and a usual spherical shape under cryo-scanning electron microscopy.

nEVs captured on NA-coated MMPs were imaged with cryo-SEM and transmission electron microscopy (TEM). We also showed that nEVs labelled with DSPE-PEG-FITC can be effectively taken up and internalized by MDA-MB-231 cells. nEV pellets were homogeneously re-suspended in serum-free medium and divided into six replicates, which served as model nEV samples. Each model sample contained approximately $1.4\times10^{9}$ nEVs, as measured using a Malvern NanoSight and on average 348.5 ng of total RNA and 189.4 ng of DNA, as determined by an Agilent Bioanalyzer and TapeStation, respectively. We first evaluated the effect of the amount of LP, ranging from 1 pmol to 10 nmol, on nEV isolation efficiency (mass fraction of RNA extracted from the captured nEVs over total nEVs). Isolation efficiency increased gradually with increasing amounts of LP, up to a maximum efficiency of 77.6% (corresponding to 10 nmol of LP). An additional quantity of LP did not further increase the isolation efficiency (FIG. 3*a*). Next, we determined the effect of incubation time on nEV isolation with 10 nmol of LP. Although there was a gently sloping increase in the average isolation efficiency with incubation time (FIG. 3*b*), prolonged incubation did not provide any statistically significant benefit (P>0.05; two-tailed t-test). For reasons of operability and reliability, we incubated the LP with nEVs for 5 min (the duration regularly employed for in vitro exosome staining via the membrane dye, PKH26). Also, we found that the incubation period with CP for maximum isolation efficiency could be shortened to 10 min with continuous gentle rotation (FIG. 3*c*). Altogether, approximately 80% of nEVs from the model sample could be labelled and isolated using 10 nmol of LP and an excess quantity of the CP, with the whole isolation procedure taking about 15 min.

Isolated nEVs provide flexibility in downstream molecular analyses. The isolated nEVs can be released from the capture probe and analyzed for detection and quantity of its contents such as nucleic acids and proteins included in the nEVs.

Figure 3D:
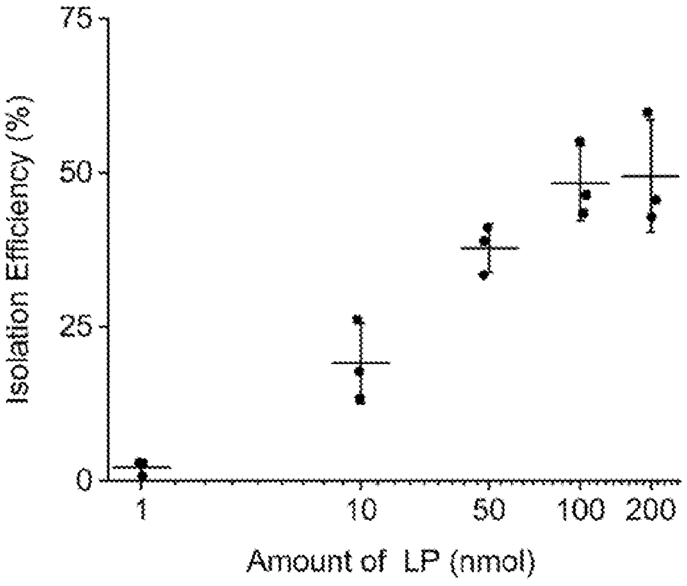

In addition, when we used DSPE-PEG-desthiobiotin as the LP, captured MDA-MB-231 nEVs on NA-coated MMPs could be released through displacement of DSPE-PEG-desthiobiotin with biotin, which binds much more tightly to NA than desthiobiotin. Approximately 84±3% of then EVs were released within 30 min. Furthermore, the released nEVs were functional. We educated non-invasive MCF7 cells with ~$8\times10^{8}$ nEVs derived from highly aggressive MDA-MB-231 cells. A wound-healing assay showed the wound-closure rate of MCF-7 cells to be about twofold faster after nEV education (P<0.05; two-tailed t-test), which indicates that the LP-labelled nEVs can induce higher levels of migration than uneducated MCF-7 cells. We then used the LP system to isolate nEVs from blood plasma. Because albumin might interfere with insertion of the LP into the membranes of nEVs, we increased the quantity of LP to 200 nmol for labelling and isolation of nEVs from 100 µl of blood plasma from a healthy human donor containing approximately 13.2 ng RNA, as determined by a Qubit fluorometer. An isolation efficiency of 48.3% was achieved using 100 nmol of LP with the CP in excess. Doubling the LP amount only slightly increased the efficiency to 49.5% (not statistically significant; P>0.05, two-tailed t-test; FIG. 3*d*).

Figure 2:
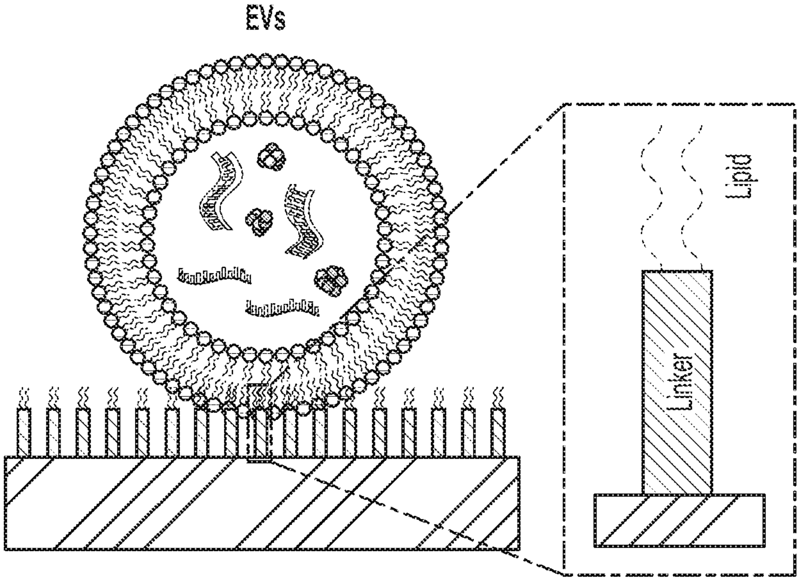
FIG. 2 illustrates a labelling probe immobilized on a surface of a substrate and a method of isolating extracellular vesicles according to one aspect of the present disclosure.
Figure 4A:
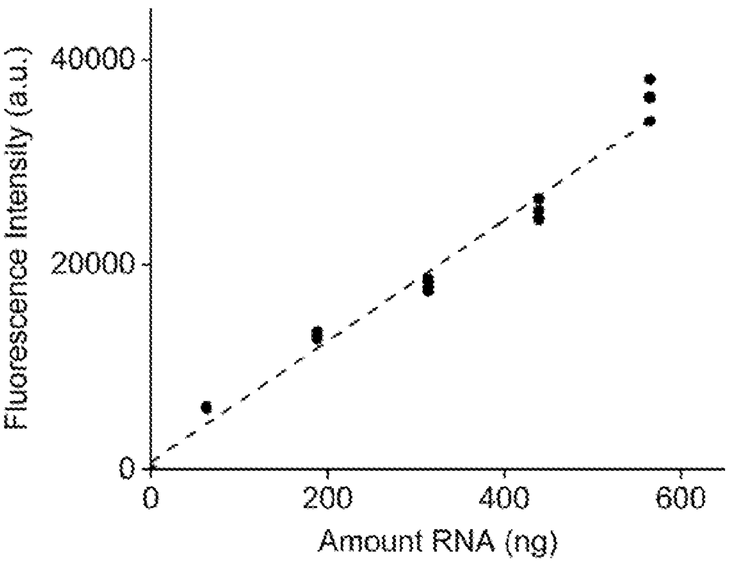
FIG. 4*a* is a plot showing fluorescence intensity to amount of RNA for LP-labelled nEVs which were enriched on NA-coated well plates followed by RNA-dye staining. The fluorescence intensity (arbitrary units, a.u.) increased in direct proportion to the total RNA contained in intact nEVs; mean±s.e.m. (n=4).

In another aspect, the lipid-based probe system can be reduced to a single component by immobilizing the LP onto a surface of a fixed substrate, e.g., FIG. 2. For example, the LP system enables nEV enrichment directly onto a surface of a substrate. Such capture and isolation onto certain substrates facilitates subsequent molecular analyses for the quantitative detection of nEVs and profiling of membrane proteins. In an embodiment, model MDA-MB-231 nEV samples were labeled with LP by contacting the nEVs with the LP for 5 min. The mixture was transferred to NA-coated wells in a multi-well plate for nEV capture. Here, NA was immobilized on the well surface of the multi-well plate, and the NA-biotin reaction time was extended to 30 min, which allowed for over 95% binding efficiency. We used a membrane-permeant dye (SYTO RNASelect) to selectively stain nEV RNA, and found that the green fluorescence intensity increased in direct proportion to the total RNA contained in intact nEVs (coefficient of determination, r2=0.98147; FIG. 4*a*). This shows that the assay can semi-quantify nEV RNA content in 35 min, which could allow it to serve as a useful alternative when nanoparticle-tracking or dynamic-light-scattering equipment is not available.

Figure 4B:
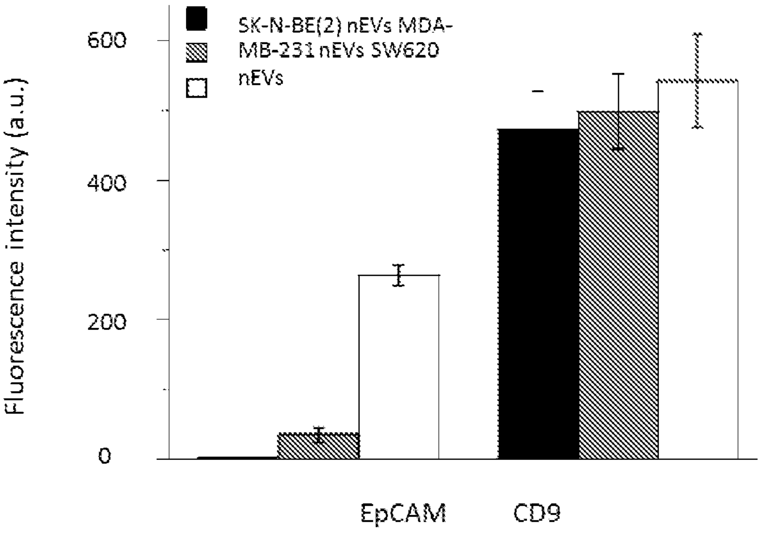
FIG. 4*b* is a plot of fluorescently labelled CD9 and EpCAM antibodies which were used to detect relevant protein expression in model nEVs released from SK-N-BE (2), MDA-MB-231 and SW620 cells. Error bars, mean±s.e.m. (n=20).

Proteins in the nEV membrane can also be detected using LP-mediated capture and enrichment. Model nEVs from SK-N-BE(2) neuroblastoma cells, MDA-MB-231 breast adenocarcinoma cells and SW620 colon adenocarcinoma cells were captured and stained with fluorescently labelled antibodies against cluster-of-differentiation molecule 9 (CD9) or epithelial cell adhesion molecule (EpCAM) (FIG. 4*b*). CD9 is one of the most ubiquitous molecular markers for all EVs, and anti-EpCAM grafted magnetic beads have been widely used for exosome isolation. EpCAM expression in nEVs from SK-N-BE(2) cells was barely detected, whereas the expression levels for nEVs from MDA-MB-231 and SW620 cells were weak and strong, respectively. In contrast, CD9 expression levels were comparable for nEVs of these three cell lines. These results parallel the EpCAM and CD9 expression levels determined by immunocytochemistry.

Nanoscale extracellular vesicles can also be directly collected by CPs, followed by the extraction and analysis of protein and nucleic-acid cargo contents. CD63 (a commonly used EV marker) and glyceraldehyde 3-phosphate dehydrogenase (GAPDH; a well-known housekeeping protein) extracted from MDA-MB-231 cell lysates and nEV protein lysates, respectively, were detected by western blot. Additionally, DNA and RNA were extracted from isolated MDA-MB-231 nEVs followed by agarose gel electrophoresis to confirm the presence of RNA and long fragments of DNA.

We also compared the contents of nEVs collected by ultracentrifugation versus those collected by an LP system. DNA from MDA-MB-231 nEVs and cellular genomic DNA without amplification were analyzed by next-generation sequencing (NGS). The purified nEV DNA samples mainly contained DNA fragments longer than 10 kbp. This differs from circulating cell-free DNA, which shows a typical apoptotic DNA ladder. The percentage of reads mapped to the human genome was 99.6% and 99.5% in the ultracentrifugation and LP system groups, respectively. DNA from nEVs isolated by the two methods uniformly spanned all chromosomes. The nEV DNA contents after ultracentrifugation and LP system isolation were similar, with a Pearson correlation coefficient of 0.96 calculated using a 100-kbp window size. The nEV DNA content extracted by either of the two methods resembles nuclear genomic DNA from the same cell line, as indicated by the copy-number-variation (CNV) plots of the purified nEV samples and of the genomic DNA sample. In addition, the Pearson correlation coefficient between the nEV DNA content from ultracentrifugation and the genomic DNA content was 0.87, and that between the nEV DNA content from the LP system and the genomic DNA content was 0.92.

Furthermore, cargo content RNA was extracted from nEVs isolated by ultracentrifugation of an LNP system, and then compared. For this data, the LP used to label the nEVs was DSPE-PEG-biotin and the capture probe was Avidin coated magnetic beads. Quadruplicated samples of MDA-MB-231 nEV RNA, including messenger RNA and microRNA, were analysed by NGS. The average percentage of reads mapped to human total RNA was 89.3% and 86.2% for the ultracentrifugation and LP system groups, respectively. In a Euclidean-distance plot of mRNA from MDA-MB-231 nEVs, the biological replicates isolated with the LP system and those isolated by ultracentrifugation appeared in separate clustered regions. Using read counts of mapped sequences, we then quantified the RNA cargo of nEVs isolated from MDA-MB-231 cells with the LP system and with ultracentrifugation. nEVs isolated from MDA-MB-231 cells contained diverse cargo RNA, including significant amounts of long intergenic noncoding RNA, ribosomal RNA, small nucleolar RNA and other RNA types in addition to the most abundant RNA type, protein-coding RNA or mRNA. There were no noticeable differences in RNA species between nEVs isolated by the LP system and those isolated by ultracentrifugation; in fact, there was a substantial overlap of mRNA (81%) and miRNA (94%) species in the top 1,000 expressed mRNAs and miRNAs. In a Bland-Altman plot comparing the expression levels of mRNAs isolated by ultracentrifugation or the LP system, we found that the majority of the detected mRNAs had similar expression levels, which was also indicated by the linear correlation coefficients of >0.998 for total RNA content. A recent report indicated that foetal bovine serum (FBS)-derived miRNAs interfere with subsequent transcription analysis. We however found minimal interference by the reported top 14 FBS miRNAs when comparing the numbers of miRNAs in the ultracentrifugation nEV samples with those in the LP system nEV samples (see Table 1 below).

TABLE 1

Comparison of miRNAs from ultracentrifugation and LNP isolated nEVs to the most abundant miRNAs from FBS-carried EVs, as detected by RNA-seq. The abundance ranking of reported top 14 miRNAs in FBS detected in ultracentrifugation and LNP methods, respectively.

| | FBS[1] | ultracentrifugation | LNP |
|---|---|---|---|
| miR-122-5p | 1 | 266 | 279 |
| miR-1246 | 2 | N/A | N/A |
| miR-148a-3p | 3 | 19 | 20 |
| miR-423-5p | 4 | 671 | 643 |
| miR-92a-3p | 5 | 55 | 48 |
| let-7b-5p | 6 | N/A | N/A |
| miR-379-5p | 7 | 527 | 495 |
| miR-127-3p | 8 | 708 | 684 |
| let-7a-5p | 9 | N/A | N/A |
| miR-320a | 10 | 18 | 16 |
| miR-432-5p | 11 | 3365 | 3365 |
| miR-181a-5p | 12 | 46, 51 | 45, 68 |
| miR-26a-5p | 13 | 184, 187 | 171, 206 |
| miR-320b | 14 | 312, 601 | 280, 552 |

[1]Wei, et al. Fetal Bovine Serum RNA Interferes with the Cell Culture derived Extracellular RNA. Scientific reports 6, 31175 (2016).

Furthermore, we found that after nEV isolation via the LP system, the weight ratio of protein to RNA in extracts decreased from 12.1 to 4.9, indicating that without an additional washing step our approach can eliminate on average 68.5% of total protein. Because nEV isolation via a certain LP system lead to a 22% loss of nEVs, we speculate that the removed protein were mainly of protein contaminants. In contrast, ultracentrifugation allowed the collection of 61.4% of the nEVs from a model sample, and additional wash purification by re-suspension in PBS buffer along with further ultracentrifugation reduced the overall efficiency to only 13.9%. Results from liquid chromatography-tandem mass spectrometry (LC-MS/MS) further revealed the relationship between the cargo proteins of ultracentrifuge-isolated nEVs and LNP-isolated nEVs. We compared our LC-MS/MS data with a recently published report on 30 key proteins in EVs (see Table 2 below).

TABLE 2

LC-MS/MS analyses of 30 key EVs cargo proteins isolated from MDA-MB-231 cells by ultracentrifugation and LNP, respectively, and comparison with a recently published[2] data of various fractions containing small EVs proteins sequentially isolated by ultracentrifugation and density gradient ultracentrifugation from human dendritic cells. Over 80% of them can be directly detected by LC-MS/MS.

| | | Human MDA-MB-231 cells derived nEVs | | Human dendritic cells derived small EVs prepared with ultracentrifugation followed by gradient density ultracentrifugation (published data)[2] | | | |
|---|---|---|---|---|---|---|---|
| | Protein | Ultracentrifugation | LNP | F5-100k | F3-10k | F3-100k | F5-10k |
| Proteins in dense small EVs | Albumin | ✓ | ✓ | ✓ | ✓ | ✓ | ✓ |
| | Prothrombin | ✓ | ✓ | ✓ | x | x | x |
| | Complement | ✓ | ✓ | ✓ | ✓ | x | x |
| | Fibronectin | ✓ | ✓ | ✓ | ✓ | ✓ | ✓ |
| Proteins in large EVs | Actinin-4 | ✓ | ✓ | ✓ | ✓ | ✓ | ✓ |
| | Actinin-1 | ✓ | ✓ | ✓ | ✓ | ✓ | ✓ |
| | GP96 | ✓ | ✓ | ✓ | ✓ | ✓ | ✓ |
| | Mitofilin | x | x | x | x | x | x |
| | MVP | x | ✓ | ✓ | ✓ | ✓ | ✓ |
| | eEF2 | ✓ | ✓ | ✓ | ✓ | ✓ | ✓ |
| Proteins in multiple EVs | Actin | ✓ | ✓ | ✓ | ✓ | ✓ | ✓ |
| | Tubulin | ✓ | ✓ | ✓ | ✓ | ✓ | ✓ |
| | Ezrin | ✓ | ✓ | ✓ | ✓ | ✓ | ✓ |
| | Moesin | ✓ | ✓ | ✓ | ✓ | ✓ | ✓ |
| | HSC70 | x | ✓ | x | x | x | x |
| | HSC90 | x | x | x | x | x | x |
| | HSP70 | ✓ | ✓ | ✓ | ✓ | ✓ | ✓ |
| | GAPDH | ✓ | ✓ | ✓ | ✓ | ✓ | ✓ |
| | Annexin II | ✓ | ✓ | ✓ | ✓ | ✓ | ✓ |
| | Flotillin-1 | ✓ | x | ✓ | ✓ | ✓ | ✓ |
| | MHC I | ✓ | ✓ | ✓ | ✓ | ✓ | ✓ |
| | MHC II | x | x | ✓ | ✓ | ✓ | ✓ |
| | CD9 | ✓ | ✓ | x | x | ✓ | ✓ |
| | CD63 | ✓ | ✓ | x | x | ✓ | x |
| Proteins in light small EVs | EHD4 | ✓ | ✓ | ✓ | ✓ | ✓ | ✓ |
| | Annexin XI | ✓ | ✓ | ✓ | ✓ | ✓ | ✓ |
| | ADAM10 | ✓ | ✓ | ✓ | x | ✓ | x |
| | Syntenin-1 | ✓ | ✓ | ✓ | ✓ | ✓ | ✓ |
| | TSG101 | ✓ | ✓ | x | x | ✓ | x |
| | CD81 | ✓ | x | x | x | x | x |

[2]Kowal, et al. Proteomic comparison defines novel markers to characterize heterogeneous populations of extracellular vesicle subtypes, Proceedings of the National Academy of Sciences 113, E968-E977 (2016).

We found a similar cargo-protein composition for nEVs isolated by ultracentrifugation and by an LNP system including a DSPE-PEG-biotin LP and a Avidin coated magnetic beads CP. Moreover, our results are also consistent with the work in Kowal, et al. referenced in Table 2, which used a combination of ultracentrifugation and density-gradient ultracentrifugation for small EV preparation. In addition, for 8,452 EV cargo proteins archived in the public database Vesiclepedia (www.vesiclepedia.org), we found that ~91% and ~94% of them corresponded to the cargo proteins from nEVs isolated by ultracentrifugation and by LNP, respectively. Similarly, ~94% of the EV cargo proteins reported in ref. 26 can be identified in the data-base. Also, 76 and 89 out of the top 100 proteins from Vesiclepedia were identified in the nEVs isolated by ultracentrifugation and LNP, respectively, and 96 of the 100 were identified in the nEVs of Kowal, et al. Analysis of the cellular distribution of the identified proteins showed that, for the ultracentrifugation, LP system and Kowal, et al. groups, respectively, 51.8%, 64.7% and 57.2% of the proteins localize with exosomes and 34.2%, 39.7% and 47.6% localize with lysosomes ($P<0.01$; two-tailed t-test). Finally, our MS analysis also confirmed that vimentin, cytokeratin, EGFR, and the mammary cancer stem cell marker CD44 appear in the nEVs from MDA-MB-231 cells, which agrees with the phenotype of this triple-negative and aggressively metastatic cancer cell line.

Detection of mutated DNA in nEVs isolated from blood-plasma samples from NSCLC patients. By using an LP system, we isolated nEVs from 100 μl blood-plasma samples of 19 non-small-cell lung-cancer (NSCLC) human patients. To achieve high sensitivity, we implemented mutant-enriched PCR assays for the analysis of mutations in EGFR exons 19 and 21, and a real-time PCR assay for the identification of mutations in KRAS codons 12 and 13. All PCR products were subjected to Sanger sequence analysis. After conventional PCR amplification, the desired PCR products of EGFR exon 19 and 21 and of KRAS were obtained from all samples. Sequencing analysis only identified the KRAS Gi3D mutation in the plasma sample of patient 42. Mutations were not detectable in the rest of the samples by Sanger sequencing of traditional PCR products. As the detection limit for the mutant allele fraction is about 10% for Sanger sequencing, we employed a mutant-enriched PCR assay that can reduce this limit to ~0.05%. After mutation-specific restriction-enzyme digestion and nested PCR, we found an L858R mutation in EGFR exon 21 in the plasma sample of patient 28, which we were unable to confirm by NGS using the patient's tissue sample because of the low quantity of sample available. Moreover, a deletion mutation in EGFR exon 19 was readily detected in patient 29, which matched the results of the NGS sequencing of this patient's tissue sample. We also used real-time PCR to enrich mutations in KRAS codons 12 and 13 for downstream sequencing (according to the manufacturer, the limit of detection can reach 0.0100 by targeting the mutant gene and suppressing the wild-type copy), which confirmed the KRAS G13D point mutation in the plasma sample of patient 42. A KRAS G12D mutation was detected in the plasma of patient 51, which was later verified by NGS of the patient's tissue sample. However, we failed to detect KRAS mutations in patients 25, 27 and 50 (Table 3), presumably because of their extremely low abundance in the nEVs of patient blood samples or because of a change in the mutation status over the period between the primary tissue biopsy and blood draw. All wild-type EGFR and KRAS alleles in patient tissue samples were detected as wild-type after nEV isolation via the LNP.

TABLE 3

KRAS and EGFR mutations in samples from 19 NSCLC patients.

| Patient | | | Tissue | EGFR mutation | | KRAS mutation | |
|---|---|---|---|---|---|---|---|
| number | Age | Sex | source | nEVs | Tissue | nEVs | Tissue |
| 24 | 61 | M | Lung | WT | WT | WT | WT |
| 25 | 58 | M | Small bowel | WT | WT | WT | **G12C** |
| 26 | 58 | F | Lymph node | WT | WT | WT | WT |
| 27 | 60 | F | Lung | WT | WT | WT | **G12C** |
| 28 | 90 | M | NA | **exon 21 L858R** | NA | WT | NA |
| 29 | 65 | F | Lymph node | **exon 19 Del** | **exon 19 Del** | WT | WT |
| 30 | 66 | M | Bone | WT | WT | WT | WT |
| 31 | 50 | M | Lymph node | WT | WT | WT | WT |
| 32 | 79 | F | NA | WT | NA | WT | NA |
| 36 | 65 | F | Lung | WT | WT | WT | WT |
| 37 | 82 | F | Lung | WT | WT | WT | WT |
| 42 | 70 | F | Lymph node | WT | WT | **G13D** | NA |
| 50 | 70 | M | Lymph node | WT | WT | WT | **G12V** |
| 51 | 70 | M | Pleura effusion | WT | WT | **G12D** | **G12D** |
| 52 | 74 | M | Liver | WT | WT | WT | WT |
| 54 | 53 | M | Lung | WT | WT | WT | WT |
| 55 | 86 | F | Lung | WT | WT | WT | WT |
| 56 | 72 | F | NA | WT | NA | WT | NA |
| 58 | 65 | M | Pleura effusion | WT | WT | WT | WT |

Bold text indicates detected mutations.
WT, wild type;
Del, deletion;
NA, not available To increase the clinical utility of EVs, efficient isolation and detection methods are needed. As phospholipid derivatives, PEGylated lipids have been used for the labelling and manipulation of cells and liposomes. Similarly, PEGylated lipids can also be used for nEV isolation. An advantage of an LP system approach described herein is rapid nEV isolation. A two-step isolation procedure can take a little as 15 min; existing methods require longer processing times, from 30 min to over 22 h. Also, the LP system does not require bulky and expensive instruments or delicate microfluidic devices. Moreover, the nEV isolation efficiency of the LP system is similar to that of ultracentrifugation. However, the EV isolation efficiency of ultracentrifugation depends on repeated cycles, and such additional purification steps can damage the nEVs and reduce yields from ~70% to less than 10%. In contrast, in the LP system of the resent disclosure, repetitive purification can be eliminated as ~68% of proteins can be removed by the one-step isolation process, which exerts minimal impact on downstream molecular analyses of the nEV content. Furthermore, LNP systems of the present disclosure allow qualitative and quantitative molecular analyses of nucleic acids and proteins. Overall, by significantly shortening the time of sample preparation and by providing relatively pure nEVs via isolation, the LNP system should facilitate nEV-based diagnostics.

With regards to the lipids for membrane labelling, DSPE bearing two hydrophobic fatty acid tails showed stronger non-covalent interactions with the lipid membranes of nEVs than did amphipathic cholesterol and C18 with its single hydrophobic fatty acid tail, and thus DSPE was found to display more stable retention. It is worth noting that the optimal quantity of LP and the isolation efficiency of nEVs differed between the model samples and plasma. The difference could be ascribed to the presence, in plasma, of albumin and other lipoproteins that bind to the LP; the binding constant of lipid and albumin is however only $\sim 1\times 10^{3}\ M^{-1}$ at room temperature. The size differences between nEVs that were visualized by TEM and NanoSight might arise from either the shrinkage of nEVs during fixation, or from shortcomings in NanoSight that lead to a bias towards the detection of larger EVs.

Cells secrete heterogeneous populations of nEVs with different sizes and compositions, and universal EV markers such as CD63 do not consistently appear in each individual nEV. Similarly, we found that the expression of EpCAM in nEVs collected from three different cancer cell lines varied. This might however reflect low nEV-isolation efficiency with anti-EpCAM-based immunoisolation. Conversely, the LP system of the present disclosure are unique in that all lipid vesicles are selected in the sample, thus providing antigen- and size-independent isolation. The method is therefore applicable to all nEVs regardless of size and protein composition. Overall, our genomic, transcriptomic and small-RNA studies indicate that the cargo contents of the LP system isolated nEVs are similar to those of nEVs isolated by ultracentrifugation. With low-coverage genomic sequencing, CNV profiles can be generated from purified nEV samples that are identical to those of the original cells. Not only could the DNA sequences obtained from LP systems- and ultracentrifugation-isolated nEVs be mapped to the human genome, they also contained CNV profiles that were highly similar to those of the original MDA-MB-231 cells. This may provide a way to confirm the tumour from which the nEVs originated. Read-counts-based quantitative analysis of the sequencing data revealed rich RNA content in the nEVs isolated by both LNP and ultracentrifugation. Most of the reported cellular coding and noncoding RNAs were present in the isolated nEVs. In all cases, the RNA from LP system-isolated nEVs was not significantly different to that from nEVs isolated by ultracentrifugation. Furthermore, protein LC-MS/MS analysis showed that the nEV protein compositions were similar for the two isolation methods, and our results are consistent with the Vesiclepedia database and a recently reported proteomic analysis of EV subtypes. A cellular-distribution analysis further confirmed that the LP system-isolated nEVs carried a large percentage of exosomal and lysosomal proteins. nEVs contain whole-genomic DNA, and mutated KRAS and p53 have been detected in exosomes pelleted from human patient serum.

In our cohort study of human patients with NSCLC cancer, mutation analysis of the tumour tissue revealed that at least one in four carried mutations in EGFR exons 19 and 21 or in KRAS codons 12 and 13. This is in fairly good agreement with the frequency of EGFR (~5%) and KRAS (~15%) mutations in NSCLC. We collected nEVs from NSCLC patients using LP system and extracted the genomic DNA for the detection of KRAS and EGFR mutations. Using Sanger sequencing right after traditional PCR, we only identified the KRAS G13D mutation in one patient. Improving the detection sensitivity via mutant-enriched PCR and real-time PCR, we were able to find mutations in the DNA of nEVs from three more patient samples (we should note, however, that EGFR and KRAS mutations in the tissue samples might not be identical to those in the plasma samples). A L858R mutation in EGFR exon 21 and a G13D mutation in KRAS were identified in nEV DNA from two patients (28 and 42, respectively; however, there was not enough sample available for tissue-based mutation analysis). This demonstrates the feasibility of mutation analysis in nEV DNA, and underscores the advantage of nEVs as a liquid-biopsy material, for which samples can be obtained easily and repeatedly. KRAS mutations in three patients (25, 27 and 50) were undetectable in the nEV DNA, probably because of extremely low allele fractions. Similar issues exist for mutation detection in circulating tumour DNA (ctDNA), so detection plat-forms and strategies developed for ctDNA might be adapted for nEV DNA.

Digital PCR, a sensitive tool that can detect mutations at 0.01% allele frequency, might resolve the discrepancy. It enabled the identification of KRAS mutations in 48% of ctDNA from patients with primary pancreatic cancer. By selecting exons and introns covering recurrent mutations in potential driver genes, mutations in ctDNA could also be detected in 50% of patients with stage-I NSCLC. This suggests that for clinical diagnostic applications, the analysis of nEV DNA would require careful selection of technologies and detection strategies.

In another aspect, the lipid-based probe system can be reduced to a single component by immobilizing the LP onto a surface of a fixed substrate, e.g., FIG. 2. As an example, we created a rough silica surface. The roughened surface as at a nanoscale length and was achieved using metal mask and dry etching. The feature size of the surface can be tuned in the range of 30-200 nm, which is optimal for interaction with small EVs. An amino-tagged PEGylated cholesterol, for example, can be immobilized onto nanostructured substrates for direct isolation of extracellular vesicles. The nanostructured surface was characterized and confirmed with AFM and SEM, respectively. The surface area increases ~43%, providing more loci for cholesterol immobilization and more surface area for extracellular vesicles attachment. The size of pits ranges from 30-200 nm, which can well accommodate extracellular vesicles. Amino group tagged PEGylated cholesterol in dimethylformamide can be covalently immobilized onto isothiocyanate group functionalized surface at room temperature. The contact angle before and after attachment of PEGylated cholesterol was measured. The bare nanostructured silica surface is super hydrophilic and thus the contact angle is 0. After surface grafting of PEGylated cholesterol, since cholesterol is amphipathic the contact angle increased to approximately 25°. Once extracellular vesicles move close to cholesterol functionalized surface, cholesterol can simultaneously and instantaneously insert into lipid membrane and tether extracellular vesicles onto surface.

In another aspect, the lipid-based probe system can be part of a device for isolating extracellular vesicles from a sample. The device can include a substrate surface having a labelling probe immobilized thereon, the labelling probe being configured to combine with a lipid bilayer of the extracellular vesicles and a fluid flow pathway configured to provide a flow path for a sample comprising extracellular vesicles to contact the substrate surface.

In an embodiment of such a device, a single component labelling probe can be conjugated to surfaces of beads. As beads are frequently used in liquid chromatography. These labelling probe conjugated beads can be used to pack columns of different size to fit the sample size. Such columns provide a fluid flow pathway configured to allow a flow path for a sample comprising extracellular vesicles to contact the bead surfaces. The liquid sample will flow through the packed column and EVs in the sample will be captured by the labelling probes on the beads.

For example, amino-tagged PEGylated cholesterol can be immobilized onto silica beads surface, and these beads can be assembled forming a chromatography column. In addition to silica beads, the material of the beads can also be polymer, such as agarose, cellulose, dextran, polyacrylamide, latex. By flowing samples through such a column, extracellular vesicles can interact with cholesterol and then tethered onto beads surface. The column would be able to process large amount of samples, e.g. urine samples, up to ~100 ml. After washing, the EVs can be lyzed and their contents analyzed.

Examples

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Collection of plasma samples. Normal control blood was obtained from consented donors at the Penn State General Clinical Research Center according to an institutional-review-board-approved protocol (IRB31216). Clinical samples were obtained with consent from advanced lung cancer patients at the Penn State Hershey Medical Center according to an institutional-review-board-approved protocol (IRB 40267EP). Samples were drawn into 10 ml Vacutainer K2-EDTA tubes (Becton Dickinson) from peripheral venepuncture. After centrifugation at 300 g for 5 min and then at 16,500 g for 20 min at 4° C., plasma was collected, filtered using a 0.22 μm pore filter and stored at −80° C. until processing.

Cell culture. MDA-MB-231, SW620 and SK-N-BE(2) cells were purchased from the American Type Culture Collection. All cells passed testing for *mycoplasma* contamination and were maintained in phenol-red-free-DMEM medium (Corning) supplemented with 10% (v/v) FBS, 100 units $ml^{-1}$ penicillin and 100 $\mu g ml^{-1}$ streptomycin. Cells were cultured in a humidified atmosphere of 5% CO2 at 37° C.

Preparation of model samples of nEVs. MDA-MB-231 cells were grown in nine T75 flasks (Falcon) for two to three days until they reached a confluency of 80%. Next, cells were cultured in SFM medium (Corning) for 48 h. The medium was collected and centrifuged at 300 g for 5 min followed by a centrifugation step at 16,500 g for 20 min to discard cellular detritus. Afterwards, the medium was filtered using a 0.22 μm (pore size) filter. A total of 108 ml of medium was collected and continuously ultracentrifuged at 100,000 g and 4° C. for 2 h. The nEV pellets were suspended in 200 μl of SFM. A 400 μl volume of nEVs in SFM was divided into six equal parts. Triplicate standardization samples were used to evaluate the efficiency of polymerizable lipids in the isolation of nEVs. The model samples were incubated with 10 μl of DNase I (1 units $\mu l^{-1}$; Life Technologies) or 5 μg $ml^{-1}$ RNase at 37° C. for 2 h. The supernatant was collected and stored at −80° C.

nEV cell uptake. nEVs in Diluent C were incubated with 2 μl of PKH26 dye (Sigma) in Diluent C for 5 min at 4° C. before purification by ultracentrifugation. The uptake was performed by incubating cell cultures with labelled nEVs in a 96-well plate for 2 h at 37° C. Cells were fixed with 4% paraformaldehyde at 4° C. for 10 min and stained with DAPI solution (1 μg $ml^{-1}$) at room temperature for 10 min. Images of the cells were acquired using a 40× objective lens on an Olympus IX71 microscope.

Optimization of the LNP with cells. FITC-tagged C18-PEG, DSPE-PEG and cholesterol-PEG powder were purchased from Nanocs and used without further purification. The FITC-tagged PEGylated lipids were dissolved in pure anhydrous ethanol at a final concentration of 1 mM and then stored at −80° C. Approximately 107 MDA-MB-231 cells were collected and re-suspended in either 250 μl of Diluent C or 5% human albumin in PBS. Ten nanomoles of each LP was added to 250 μl of Diluent C before being added to the cell suspension. The samples were mixed gently at 4° C. for 5 min followed by centrifugation at 500 g for 5 min to remove redundant LPs, and then fixed with 4% paraformaldehyde at 4° C. for 10 min. The cells were re-suspended in 1.5 ml of PBS, stained with DAPI solution (1 μg $ml^{-1}$) at room temperature for 10 min, thoroughly rinsed thrice with PBS and finally re-suspended in 500 μl of PBS. Cell suspension (20 μl) was added onto glass cover slips for fluorescent imaging under a 40× objective lens using an Olympus IX71 microscope. The fluorescence intensities were analysed using the ImageJ software package (National Institutes of Health).

Preparation and characterization of the CP. The magnetic Fe3O4-SiO2 core-shell submicrometre particles were synthesized via a modified Stober sol-gel process 44-48. Briefly, 30 mg of as-prepared $Fe_3O_4$ submicrometre particles were ultrasonically dispersed in a solution containing 160 ml of ethanol, 40 ml of water and 10 ml of concentrated ammonia (28% w/w). Tetraethyl orthosilicate (0.3 ml) was then added dropwise under sonication, followed by stirring for 3 h at room temperature. The resulting particles were separated using a magnet, washed thoroughly with deionized water and ethanol, and dried at 60° C. for 12 h.

To functionalize the MMPs with amino groups, 250 mg of MMPs and 250 μl of 3-aminopropyltriethoxysilane were ultrasonically dispersed in 30 ml of toluene. The mixture was refluxed for 12 h under a nitrogen atmosphere. Finally, the products were collected, thrice rinsed with toluene and ethanol, and dried at 80° C. overnight. The morphology of the particles was examined using a scanning electron microscope (Zeiss, Sigma). Fourier transform infrared spectra were obtained using a Bruker Vertex V70 over a KBr pellet and then scanned from 400-4,000 cm−1 at a resolution of 6 $cm^{-1}$.

Amine-functionalized MMPs (5 mg) were added to a dimethylformanide solution containing 10% pyridine and 1 mM phenyldiisothiocyanate for 2 h. Particles were then thoroughly washed with dimethylformanide, ethanol and deionized water. The zeta potential of the MMPs before and after chemical modification was measured using a Zetasizer (Malvern). Approximately 625 μg of NA proteins (Life Technologies) in deionized water were conjugated to isothiocyanate-grafted MMPs at 37° C. for 1 h followed by blocking with 1% BSA in PBS and washing with PBS thrice. The fresh NA-coated MMPs were immediately used for nEV isolation.

Isolation of nEVs using the LNP. LP (biotin-tagged DSPE-PEG) powder was dissolved in pure anhydrous ethanol at a final concentration of 1 mM and stored at −20° C. The nEVs were labelled with the LP according to the PKH26 labelling protocol, with minor modifications. A 100 μl volume of each nEV model sample was added to 1 ml of Diluent C. LP (0.001, 0.01, 0.1, 1, 5 or 10 nmol) was added to the other 1 ml of Diluent C before being added to the nEVs and the control. The samples were mixed gently at 4° C. for 5 min and then incubated with ~$10^{12}$ CP (NA-coated MMPs) at room temperature for 30 min. The labeled nEVs bound to the CP were isolated from the sample by a magnet. The labeled nEVs bound to the CP could also have been isolated from the sample by electrostatic force, dielectrophoretic force, gravity, and centrifugal force. After isolation, CPs were thoroughly rinsed thrice with PBS to remove non-specific molecules absorbed on the CP surface. The influence of LP mixing times from 2 to 8 min and CP incubation times from 5 to 30 min were assessed and optimized. The morphology of nEV-bound CPs was characterized using SEM.

Aliquots, comprising 1, 10, 50, 100 or 200 nmol of LP in 500 μl of Diluent C, were added to 100 μl of plasma (collected from a healthy volunteer), and then mixed for 5 min at 4° C. and incubated with CPs at room temperature for 10 min. Additionally, 100 μl of plasma was added to 30 ml PBS and ultracentrifuged once at 100,000 g and 4° C. for 2 h. RNA was extracted as before to evaluate the isolation efficiency. All experiments were performed in triplicate.

Release of captured nEVs using biotin. DSPE-PEG-desthiobiotin (Nanocs) in pure anhydrous ethanol was prepared as above. Following the above-mentioned protocol, nEVs were labelled with DSPE-PEG-desthiobiotin and captured onto CPs. Surplus uncaptured nEVs were removed by rinsing the CPs thrice with PBS. Twenty nanomoles of biotin in PBS was introduced to displace the DSPE-PEG-desthiobiotin. After incubation for 30 min at room temperature, CPs were thoroughly washed with PBS using a pipette. The supernatant was collected for RNA extraction. Release efficiency was calculated as the amount of RNA extracted from the supernatant (released nEVs) divided by the total amount of RNA from captured nEVs.

Characterization of nEVs. For TEM, 5 μl of model nEV sample was placed on a 400-mesh Formvar-coated copper grid and incubated for 3 min at room temperature. Excess samples were blotted with filter paper and then negatively stained with filtered aqueous 1% uranyl acetate for 1 min. Stain was blotted dry from the grids with filter paper, and samples were allowed to dry. Samples were then examined in a FEI Tecnai transmission electron microscope at an accelerating voltage of 100 kV.

For SEM, model nEV samples (5 μl) were seeded onto a poly-l-lysine-coated silicon wafer and fixed in 4% paraformaldehyde for 3 h. The samples were then sequentially immersed in 20, 30, 50, 70, 85, 95 and 100% ethanol solutions for 15 min per solution. Samples were lyophilized overnight followed by sputter-coating with gold at room temperature. The morphology of the nEVs was examined under a Zeiss field-emission scanning electron microscope.

For cryo-EM, 5 μl of model nEV sample was added to a 200-mesh grid (Quantifoil, Ted Pella), blotted for 1 s with FEI Vitrobot before plunging into liquid ethane, and transferred to a cryo-sample holder. Samples were visualized by TEM (FEI Tecnai F20) and SEM (FEI Helios NanoLab 660). The number of nEVs was measured using a Nanosight LM10 (Malvern). nEVs were diluted 1:100, placed in the chamber, and analysed using Nanoparticle Tracking Analysis software (Malvern) to count the number of nEVs.

Wound-healing assay. Approximately 3×105 MCF-7 cells were seeded into each well of a 24-well plate and were allowed to attach onto the substrate overnight. When confluence reached 100%, a pipette tip was used to scratch the cell monolayer. Detached cells were removed by replacing the medium. Cells were then incubated at 37° C. in 5% CO2. To educate cells with nEVs, ~$8\times10^8$ released MDA-MB-231 nEVs were added. The width of the wound was monitored under the microscope at 0, 24 and 48 h time points. ImageJ was used to calculate the wound area.

Rough estimation of RNA quantity in nEVs using SYTO RNASelect stain.

Aliquots of 0, 5, 15, 25, 35 and 45 μl of model nEV sample were mixed with 5 μl of 500 nM SYTO RNASelect stain (Life Technologies). The final volume of the solution was brought to 50 μl with PBS followed by incubation at 37° C. for 20 min. The excitation and emission wavelengths for green fluorescence measurement were at 490 and 530 nm, respectively, using a plate reader. In the other group, RNA was extracted from equal amount of nEVs samples. A standard curve of fluorescence from RNA quantity was then constructed. Pre-warmed labelling solution (5 μl) was applied to 50 μl samples and incubated for 20 min at 37° C. When labelling was complete, the fluorescence intensity of each sample was directly measured in a plate reader without rinsing.

nEV membrane-protein detection using an ELISA-like assay. Approximately $10^{11}$ nEVs from each of three cell types, SK-N-BE(2), MDA-MB-231 and SW620, were re-suspended in 100 μl of SFM and labelled with 5 nmol of LP following the above protocol. nEVs were directly anchored onto an NA-coated glass substrate after incubation at room temperature for 30 min. All samples were fixed with stabilizing fixative (BD, Biosciences) for 10 min followed by three rinses with PBS. The surface was blocked with 1% BSA in PBS for 30 min at room temperature and incubated overnight at 4° C. with fluorophore-conjugated antibodies against CD9 (Santa Cruz Biotechnology, sc-13118 FITC) and CD326 (EpCAM; Miltenyl Biotec, 130-098-115). Afterwards, samples were thoroughly washed with PBS and observed under a fluorescence microscope (Olympus). The fluorescence intensity was quantified using ImageJ.

Nucleic acid and protein extraction. RNA preparation was conducted using Trizol (Life Technologies) according to the manufacturer's instructions. Trizol (750 μl) and chloroform (200 μl) were added to and vigorously mixed with nEVs. After centrifugation, the aqueous phase of the sample was homogenized with 500 μl of pure isopropanol and pelletized. This was followed by an RNA wash using 1 ml of 75% ethanol. Finally, the RNA pellet was dissolved in 50 μl of RNase-free water. The RNA concentration in the nEVs was measured using a Qubit Fluorometer (Life Technologies) or an Agilent 2100 Bioanalyzer.

The DNA was extracted using the QIAamp DNA micro kit (Qiagen, Germany) according to the manufacturer's instructions. Briefly, to conduct DNA extraction from nEVs, 10 μl of proteinase K and 100 μl of lysis buffer were added. After heat inactivation at 56° C. for 10 min, 100 μl of pure ethanol was added. The whole volume was centrifuged in a spin column. After two washing steps, the DNA was eluted in 50 μl of AE buffer and stored at −20° C. until PCR amplification.

The amount of protein re-suspended in modified RIPA buffer was determined using a Micro BCA protein assay kit (Pierce). Isolated nEVs were mixed well with working reagent and incubated at 60° C. for 30 min. The fluorescence intensity of each sample was measured using an Infinite M200 Pro plate reader. The protein concentration for each nEVs sample was determined using a BSA standard curve.

To monitor nEV expression of GAPDH and CD63, isolated nEVs were collected in 8 M urea, 2.5% SDS, 5 μg $ml^{-1}$ leupeptin, 1 μg $ml^{-1}$ pepstatin and 1 mM phenylmethylsulfonyl fluoride buffer. The amount of protein was measured according to the Micro BCA kit instructions and analysed using acrylamide gels. Wet electrophoretic transfer was used to transfer the proteins in the gel onto polyvinylidene difluoride membranes (Immobilon-P). The protein blot was blocked for 1 h at room temperature with 5% non-fat dry milk in PBS and 0.05% Tween 20, and then incubated overnight at 4° C. with primary antibodies against GAPDH (Abeam, ab9485) and CD63 (Santa Cruz Biotechnology, sc-15363). Afterwards, secondary antibodies were incubated for 1 h at room temperature. Samples were washed thrice with PBS and 0.05% Tween 20 for 10 min. Blots were visualized using chemiluminescence (Pierce).

PCR and sequencing. KRAS analysis (466 bp) was performed using the following primers: SEQ ID NO: 1 (forward 5'-AAG GCC TGC TGA AAA TGA CTG-3') and SEQ ID NO: 2 (reverse 5'-TCA CAA TAC CAA GAA ACC CAT-3') (Kahlert, et al. J. Biol. Chem. 289, 3869-3875 (2014)). Analysis of EGFR Exons 19 and 21 was performed using the following primers: Exon 19 (372 bp), SEQ ID NO: 3 (forward 5'-GCA ATA TCA GCC TTA GGT GCG GCT C-3'), SEQ ID NO: 4 (reverse 5'-CAT AGA AAG TGA ACA TTT AGG ATG T G-3'); Exon 21 (300 bp), SEQ ID NO: 5 (forward 5'-TGC AGA GCT TCT TCC CAT GA-3'), SEQ ID NO: 6 (reverse 5'-GCA TGT GTT AAA CAA TAC AGC-3'). PCR was performed in a 25 μl reaction tube containing 12.5 μl of GoTaq Green Master Mix (Promega), 10.5 μl of template DNA, and 1 μl of each primer. Amplification was carried out under the following conditions: 94° C. for 1 min, two cycles of 94° C. for 10 s, 67° C. for 10 s, 70° C. for 10 s; two cycles of 94° C. for 10 s, 64° C. for 10 s, 70° C. for 10 s; two cycles of 94° C. for 10 s, 61° C. for 10 s, 70° C. for 10 s; 55 cycles of 94° C. for 10 s, 60° C. for 10 s, 70° C. for 10 s, endless 4° C. PCR products were cleaned using a QIAquick PCR Purification Kit (Qiagen) following the manufacturer's instructions, and then sequenced by Sanger DNA sequencing (Applied Biosystems 3730XL) at the Genomics Core Facility of Penn State University.

Alternatively, a PointMan KRAS (codon 12 or 13) DNA enrichment kit (EKF molecular diagnostics), a real-time PCR kit, was used to enrich mutations. Relevant samples were purified for Sanger sequencing once variant traces were observed in the real-time PCR. For the EGFR-mutant-enriched PCR assay, 2 μl of the first traditional PCR products of EGFR exon 19 and exon 21 were further digested with Mse I and Msc I, respectively, at 37° C. for 4 h. An aliquot was used as a template for the second round of nest PCR amplification under the same conditions as the first round PCR but for 42 cycles. The exon 19 nest PCR (175 bp) primers were: SEQ ID NO: 7 (forward 5'-TAA AAT TCC CGT CGC TAT CAA-3') and SEQ ID NO: 8 (reverse 5'-ATG TGG AGA TGA GCA GGG-3'). The exon 21 nest PCR (213 bp) primers were: SEQ ID NO: 9 (forward 5'-CAG CAG GGT CTT CTC TGT TTC-3') and SEQ ID NO: 10 (reverse 5'-GAA AAT GCT GGC TGA CCT AAA G-3'). Products were purified and analysed by Sanger DNA sequencing.

Whole genome NGS. The isolated nEV DNA was mechanically fragmented to 400 bp using a focused ultrasonicator (Covaris). DNA sequencing was performed at the Biopolymers Facility at Harvard Medical School. The WaferGen DNA prepX kit was used to prepare the sequencing library. NGS was performed using an Illumina NextSeq 500 platform (paired-end 2×77 bp) to a coverage depth of 3.3×. The data quality was assessed using FastQC (Babraham Bioinformatics). Data was mapped to the human genome (hg38) using bwa-mem (v.0.7.12) and coverage files were produced using Bedtools (v.2.17.0). Mapping was visualized using IGV, and read counts in 10 kbp bins were calculated with Bedtools. Read coverage in the 10 kbp bins was plotted in circus plots for each sample. To determine the CNV of the nEV samples, each NGS dataset was down sampled to 10 Mbp. Separately, genomic DNA of the same cell line was prepared without amplification and sequenced by NextSeq to a coverage depth of 0.16×. The CNV plots were generated using the open-source web platform Gingko.

NGS of RNA. The ribosomal RNA-depleted total nEV RNA was extracted using a miRNeasy Mini Kit (Qiagen). RNA sequencing was performed at the Genomics Technology Center at New York University medical center. An llumina TruSeq Strandard mRNA kit was used to prepare the mRNA and sRNA sequencing libraries. Sequencing libraries were pooled together and sequenced on the Illumina HiSeq platform (single-end 50 bp). We obtained more than 20 million 51-bp reads for each of the 16 samples (small RNA-seq, n=8; total RNA-seq, n=8). The adapters for small RNA-seq were removed using cutadapt (v.1.3). All the reads were mapped to the human reference genome (GRCh37/hg19) using STAR aligner (v.2.3.0e r291). The alignment was guided by a Gene Transfer File (GTF version GRCh37.70). The reads per million normalized BigWig files were generated using Bedtools (v.2.17.0) and the bedGraphToBigWig tool (v.4). Read count tables were generated using HTSeq (v.0.6.0)60 based on the Ensembl gene annotation file (Ensembl GTF version GRCh37.70). All read-count tables were then corrected for their library-size differences based on their geometric library-size factors calculated using the DESea2 R package (v.3.0), and differential expression analysis was performed. To compare the level of similarity among the samples in our dataset on the basis of their normalized gene expression, we used Euclidean-distance-based sample clustering. All downstream statistical analyses and data visualizations were performed in R (v.3.1.1; R Foundation). For principal component analysis and Euclidean distance analyses, we transformed the normalized count data using DESeq2's rlogTransformation function for fixing for infinite log 2 (expression values) in genes with zero (or not detected) expression. We employed DESeq's plotPCA function to calculate the first two principal components, and we created the two-dimensional plot using the ggplot2package (v.2.0.0). For distance analysis, we used the R dist function to calculate the sample distances in the transformed normalized count data (as explained earlier) by setting the method as Euclidean (default), clustering the samples on the basis of their distance, and visualizing them in heat maps.

LC-MS/MS. Protein concentrations were measured by BCA-protein assay. Approximately 30 μg of proteins were separated by SDS-PAGE using 10% Bis-Tris Nupage gels (Life Technologies). Serial gel slices were excised and diced into smaller fragments. Samples were reduced with 10 mM dithiothreitol in 25 mM NH4HCO3 at 56° C. for 1 h and alkylated with 55 mM iodoacetamide for 45 min at room temperature. In-gel trypsin digestion was performed using 10 ng $\mu l^{-1}$ of sequencing grade modified porcine trypsin (Promega) diluted in 505 mM NH4HCO3 at 37° C. overnight. Peptides were extracted with 0.5% formic acid and 50% acetonitrile. Following evaporation of acetonitrile, peptides were purified using a ZipTipC18 column (Millipore). The volume of each eluted sample was reduced in a Speed-vac (Savant, Thermo Fisher) to 5 μl in order to evaporate acetonitrile, and then adjusted to 20 μl with 0.1% formic acid prior to LC-MS/MS analysis. An AB SCIEX TripleTOF 5600 System (Foster City) equipped with an Eksigent nanoLC Ultra and ChiPLC-nanoflex (Eksigent) in the trap elute configuration was employed for LC-MS/MS. The acquired mass spectrometric raw data was processed using ProteinPilot 5.0 software (AB SCIEX) via the Paragon search mode. The ProteinPilot Descriptive Statistics Template (AB SCIEX) was used for alignment of multiple results and evaluation of the false discovery rate.

Additional details for the above procedures can be found in Wan, Y. et al. Rapid magnetic isolation of extracellular vesicles via lipid-based nanoprobes. Nat. Biomed. Eng. 1, 0058 (2017).

In summary, the Examples provide a lipid nanoprobe system for the rapid isolation of nEVs, including exosomes from a serum-free cell-culture supernatant sample and from a blood plasma sample. The Examples involved the labelling of the lipid bilayer of nEVs with biotin-tagged 1,2-distearoyl-sn-glycero-3-phosphethanolamine-poly(ethyleneglycol) (DSPE-PEG).

The labelled nEVs were then be collected by NA-coated magnetic sub-micrometre particles (MMPs), for subsequent extraction and analyses of nEV cargo. Compared with differential centrifugation (the most prevalent method for nEV isolation), the LP system shortens the isolation procedure from hours to 15 minutes and does not require bulky or expensive equipment. It is also highly flexible and can be adopted for various downstream analyses of DNA, RNA and proteins. We applied the LP system to obtain nEV DNA from 19 stage-IV non-small-cell lung-cancer (NSCLC) patients, which allowed us to detect mutations in KRAS (V-Ki-ras2 Kirsten rat sarcoma viral oncogene homologue) codons 12 and 13 and EGFR (epidermal growth factor receptor) exons 19 and 21.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A method of isolating extracellular vesicles from a sample, the method comprising:

contacting at least one labelling probe with a sample comprising extracellular vesicles having a lipid bilayer, wherein each labelling probe comprises a lipid tail, a spacer, and a tag and the lipid tail of the labelling probe inserts into the lipid bilayer of at least one of the extracellular vesicles so as to label the extracellular vesicle and facilitate capturing of the labeled extracellular vesicle, the sample including a fluid having the extracellular vesicles, the fluid being a body fluid, a buffer fluid, or a cell culture fluid, the extracellular vesicles being included in the fluid such that:

(a) there is a ratio of $1.4\times10^9$ extracellular vesicles to at least 10 nanomoles (nmol) of the labeling probe during the contacting when the fluid is the body fluid, (b) there is a ratio of $1.4\times10^9$ extracellular vesicles to at least 0.1 nmol of the labeling probe during the contacting when the fluid is the cell culture fluid, and (c) there is a ratio of $1.4\times10^9$ extracellular vesicles to at least 1 nmol of the labeling probe during the contacting when the fluid is the buffer fluid;

capturing the at least one labeled extracellular vesicle with a capture probe configured to combine with the at least one labelling probe, the capture probe comprising a magnetic particle or a magnetic bead having a compound that binds the tag of the labelling probe to the capture probe; and isolating the at least one labeled extracellular vesicle captured with the capture probe via at least one magnetic field.

2. The method of claim 1, further comprising releasing the labeled extracellular vesicles from the capture probe.

3. The method of claim 1, wherein the compound that binds the tag to the capture probe is a protein or an antigen.

4. The method of claim 1, wherein the compound that binds the tag to the capture probe coats the magnetic particle or the magnetic bead.

5. The method of claim 1, wherein the lipid tail comprises a fatty acid, glycerolipid, glycerophospholipid, sterol lipid, phingolipid, saccharolipid, eicosanoid, their derivatives, or any combination thereof.

6. The method of claim 1, wherein the spacer comprises a polyethylene glycol, the tag comprises biotin, and the magnetic field is provided via a magnet.

7. A method of analyzing contents of extracellular vesicles, the method comprising:

isolating the extracellular vesicles according to claim 1;

extracting contents from the isolated extracellular vesicles; and analyzing a structure and/or a function of the extracted contents.

8. The method of claim 1, wherein the at least one labeled extracellular vesicle is isolated regardless of a protein composition of the extracellular vesicles.

9. The method of claim 1, wherein the lipid tail of the labeling probe comprises a phospholipid.

10. The method of claim 9, wherein the phospholipid comprise a glycerophospholipid.

11. The method of claim 1, wherein the contacting and the capturing takes between 7 minutes and 38 minutes.

12. The method of claim 1, wherein the isolating comprises using a magnet to apply the magnetic field to attract the magnetic particle or the magnetic bead to the magnet.

13. The method of claim 1, wherein the fluid is the body fluid and there is a ratio of $1.4\times10^9$ extracellular vesicles to at least 100 nmol of the labeling probe during the contacting.

14. The method of claim 13, wherein the body fluid is blood, plasma or urine.

15. The method of claim 1, wherein the fluid is the cell culture fluid or the buffer fluid and there is a ratio of $1.4\times10^9$ extracellular vesicles to at least 1 nmol of the labeling probe during the contacting.

16. The method of claim 1, wherein the fluid is the cell culture fluid or the buffer fluid and there is a ratio of $1.4\times10^9$ extracellular vesicles to at least 5 nmol of the labeling probe during the contacting.

17. The method of claim 1, wherein the fluid is the body fluid and there is a ratio of $1.4\times10^9$ extracellular vesicles to at least 50 nmol of the labeling probe during the contacting.

18. The method of claim 1, wherein the isolating is performed without utilization of ultracentrifugation.

19. The method of claim 14, wherein the body fluid is blood.

* * * * *